(12) United States Patent
Hossainy et al.

(10) Patent No.: US 8,029,816 B2
(45) Date of Patent: *Oct. 4, 2011

(54) MEDICAL DEVICE COATED WITH A COATING CONTAINING ELASTIN PENTAPEPTIDE VGVPG

(75) Inventors: Syed Faiyaz Ahmed Hossainy, Hayward, CA (US); Yiwen Tang, San Jose, CA (US); Lothar W. Kleiner, Los Gatos, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1029 days.

This patent is subject to a terminal disclaimer.

(21) Appl. No.: 11/803,031

(22) Filed: May 10, 2007

(65) Prior Publication Data

US 2008/0038310 A1 Feb. 14, 2008

Related U.S. Application Data

(63) Continuation-in-part of application No. 11/449,896, filed on Jun. 9, 2006.

(51) Int. Cl.
| | |
|---|---|
| *A61F 2/00* | (2006.01) |
| *A61K 9/00* | (2006.01) |
| *A61K 38/43* | (2006.01) |
| *A61K 38/44* | (2006.01) |
| *A61K 38/00* | (2006.01) |
| *C12N 11/04* | (2006.01) |

(52) U.S. Cl. ...... 424/423; 424/400; 424/94.1; 424/94.4; 435/182; 514/2

(58) Field of Classification Search .......... None
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | |
| 5,019,096 A | 5/1991 | Fox, Jr. et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,250,516 A * | 10/1993 | Urry | 514/17 |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,306,786 A | 4/1994 | Moens et al. | |
| 5,328,471 A | 7/1994 | Slepian | |
| 5,330,768 A | 7/1994 | Park et al. | |
| 5,336,256 A * | 8/1994 | Urry | 623/1.44 |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,485,496 A | 1/1996 | Lee et al. | |
| 5,514,380 A * | 5/1996 | Song et al. | 424/426 |
| 5,516,881 A | 5/1996 | Lee et al. | |
| 5,569,463 A | 10/1996 | Helmus et al. | |
| 5,578,073 A | 11/1996 | Haimovich et al. | |
| 5,584,877 A | 12/1996 | Miyake et al. | |
| 5,605,696 A | 2/1997 | Eury et al. | |
| 5,607,467 A | 3/1997 | Froix | |
| 5,609,629 A | 3/1997 | Fearnot et al. | |

(Continued)

FOREIGN PATENT DOCUMENTS

| | | |
|---|---|---|
| DE | 42 24 401 | 1/1994 |

(Continued)

OTHER PUBLICATIONS

International Search Report for PCT/US2007/013687, mailed Jul. 30, 2008, 16 pgs. Morelli et al., "Structure-activity relationships for some elastin-derived peptide chemoattractants", J. of Peptide Res. vol. 49, No. 6, pp. 492-499 (1997).

Wright et al., "Thermoplastic Elastomer Hydrogels via Self-Assembly of an Elastin-Mimetic Triblock Polypeptide", Adv. Funct. Mater vol. 12, No. 2, pp. 149-154 (2002).

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

(Continued)

*Primary Examiner* — David Naff

(74) *Attorney, Agent, or Firm* — Squire, Sanders & Dempsey (US) LLP

(57) ABSTRACT

The present invention is directed to medical devices including coatings. The coatings include a topcoat which includes a copolymer comprising a block of an elastin pentapeptide. The topcoat is over a layer of poly(vinyl alcohol) on a hydrophobic coating or over a porous coating comprising pores or depots that include a bioactive agent.

25 Claims, 4 Drawing Sheets

U.S. PATENT DOCUMENTS

| | | | |
|---|---|---|---|
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,475,779 B2 | 11/2002 | Mathiowitz et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,613,432 B2 | 9/2003 | Zamora et al. |
| 6,616,765 B1 | 9/2003 | Hossaony et al. |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,641,611 B2 | 11/2003 | Jayaraman |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |

| | | |
|---|---|---|
| 6,673,154 B1 | 1/2004 | Pacetti et al. |
| 6,673,385 B1 | 1/2004 | Ding et al. |
| 6,689,099 B2 | 2/2004 | Mirzaee |
| 6,689,350 B2 | 2/2004 | Uhrich |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Falotico et al. |
| 6,780,424 B2 | 8/2004 | Claude |
| 6,790,228 B2 | 9/2004 | Hossainy et al. |
| 6,824,559 B2 | 11/2004 | Michal |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 6,926,919 B1* | 8/2005 | Hossainy et al. .............. 427/2.25 |
| 7,008,667 B2 | 3/2006 | Chudzik et al. |
| 7,601,383 B2* | 10/2009 | Kleiner et al. ................. 427/2.1 |
| 2001/0007083 A1 | 7/2001 | Roorda |
| 2001/0029351 A1 | 10/2001 | Falotico et al. |
| 2001/0037145 A1 | 11/2001 | Guruwaiya et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0171545 A1* | 9/2004 | Chaikof et al. ................. 514/12 |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| EP | 1 422 242 | 5/2004 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |

| | | |
|---|---|---|
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/45941 | 9/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nagapudi et al., *Viscoelastic and mechanical behavior of recombinant protein elastomers*, Biomaterials 26, pp. 4695-4706 (2005).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Reiersen et al., *Short Elastin-like Peptides Exhibit the Same Temperature-induced Structural Transitions as Elastin Polymers: Implications for Protein Engineering*, J. Mol. Biol. 283, pp. 255-264 (1998).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

va Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Val Gly Val Pro Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Ser Ile Lys Val Ala Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Tyr Ile Gly Ser Arg Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: Sequence repeats indefinitely

<400> SEQUENCE: 4

Leu Gly Gly Val Gly
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: Sequence repeats indefinitely

<400> SEQUENCE: 5

Val Pro Gly Val Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Val Pro Gly Val Gly
1               5
```

US 8,029,816 B2

MEDICAL DEVICE COATED WITH A COATING CONTAINING ELASTIN PENTAPEPTIDE VGVPG

CROSS-REFERENCE TO RELATED APPLICATION

This is a continuation-in-part application of U.S. application Ser. No. 11/449,896, filed on Jun. 9, 2006, the teaching of which is incorporated herein in its entirety.

SEQUENCE LISTING

This application incorporates by reference the material in the ASCII text file "SEQ.txt" of 1437 bytes created on Oct. 27, 2010.

BACKGROUND OF THE INVENTION

1. Field of the Invention

This invention generally relates to elastin-based copolymers for coating an implantable device such as a drug delivery stent or for forming a composition as cell therapy carrier.

2. Description of the Background

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

The existing polymeric coating on a stent can have different types of limitations. For example, some poly(ester amide) based coatings can have poor mechanical properties so as to compromise coating integrity, and coating based on hydrophobic polymers can have problems in controlling release of a hydrophilic drug.

Therefore, there is a need for new carrier materials for controlled delivery of an agent. There is a further need for coating materials for coating a medical device. There is also a need for polymers such as protein polymers that bioabsorb through a dissolution mechanism which are more vascularly biocompatible than synthetic polymers The polymer and methods of making the polymer disclosed herein address the above described problems.

SUMMARY OF THE INVENTION

Described in this invention is an elastin-based copolymer. The copolymer can be used to form a coating on a medical device. In some embodiments, the coating can further include a polymer, a biobeneficial material, a bioactive agent, or combinations of these. Some examples of the bioactive agent include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, bioactive RGD, CD-34 antibody, abciximab (REOPRO), progenitor cell capturing antibody, prohealing drugs, growth factor vascular endothelial growth factor (VEGF), prodrugs thereof, co-drugs thereof, or a combination thereof. In some embodiments, the coating can include a combination of two drugs, such as both an anti-proliferative and an anti-inflammatory.

In some embodiments, the elastin-based copolymer can be used as hydrogel-like scaffold. For example, one can use it as cell delivery using a depot platform. In some embodiments, a matrix including the polymer described herein can be injected into depots that sit on a carrier platform such as depot stents.

A medical device having a coating or depot platform described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, and combinations thereof.

DETAILED DESCRIPTION OF THE INVENTION

Figure 1:
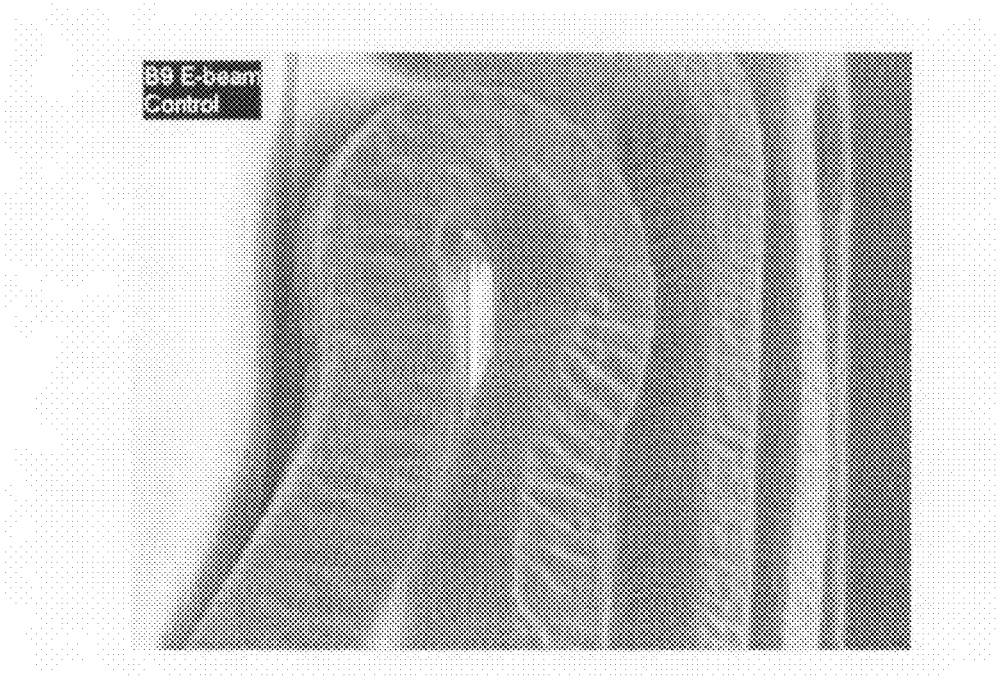
FIG. 1 shows that B-9 coating is crimping/icy hot onto catheters, followed after E-beam.

Described in this invention is an elastin-based copolymer. The copolymer can be used to form a coating on a medical device. In some embodiments, the coating can further include a polymer, a biobeneficial material, a bioactive agent, or combinations of these. Some examples of the bioactive agent include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, bioactive RGD, CD-34 antibody, abciximab (REOPRO), progenitor cell capturing antibody, prohealing drugs, growth factors such as vascular endothelial growth factor (VEGF), prodrugs thereof, co-drugs thereof, or a combination thereof. In some embodiments, the coating can include a combination of two drugs, such as both an anti-proliferative and an anti-inflammatory.

In some embodiments, the elastin-based copolymer can be used as hydrogel-like scaffold. For example, one can use it as cell delivery using a depot platform. In some embodiments, a matrix including the polymer described herein can be injected into depots that sit on a carrier platform such as depot stents.

As used herein, the term "elastin-based copolymer" is sometimes referred to as the "elastin-based polymer". These two terms can be used interchangeably. Other names include protein elastomer, protein polymer, protein tri-block copolymer, and elastin mimetic.

A medical device having a coating or depot platform described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, and combinations thereof.

Elastin-Based Polymer

Elastin is a protein that is found in the walls of arteries, in lungs, intestines and skin in the body of an animal. Elastin imparts elasticity to the body. Working in partnership with collagen, elastin allows the body organs to stretch and relax. Thus, while collagen provides rigidity, elastin allows the blood vessels and heart tissues, for example, to stretch and then revert to their original positions, i.e. to recoil. Therefore, elastin provides for structural integrity and for the compliance of the vessel at low pressure whereas collagen gives the tensile resistance required at high pressures.

Elastin is found to contain short peptides. The most frequent pentapeptide sequence is valyl-glycyl-valyl-prolyl-glycine (VGVPG) (SEQ ID NO: 1). VGVPG (SEQ ID NO: 1) is found to exhibit elastin-like properties (see, e.g., Reiersen, H., et al., J. Mol. Biol. 283:255-264 (1998)). See also: Biomaterials 26 (2005) 4695-4706.

In some embodiments, the elastin-based polymer described herein can be an ABA or BAB type polymer, where A represents a unit that includes the pentapeptide sequence VGVPG (SEQ ID NO: 1) and B represents a unit which can be a peptide sequence or a unit derived from a monomer. The copolymer can be a block or random copolymer. Commonly the BAB block copolymers are comprised such that the B-block is hydrophobic while the A-block is more hydrophilic.

In some embodiments, the elastin-based copolymer is an ABA triblock copolymer, where A is a block comprising the VGVPG (SEQ ID NO: 1) sequence and B is a block derived from a peptide or monomer(s). In some embodiments, B can be a hydrophilic variant of the VGVPG (SEQ ID NO: 1) peptide. The term "variant" refers to any form of VGVPG (SEQ ID NO: 1) modification. For example, an amino acid in the peptide can be replaced with another amino acid. In some embodiments, the sequence of VGVPG (SEQ ID NO: 1) can be varied so as to form a variant of the VGVPG (SEQ ID NO: 1) peptide. In some embodiments, the VGVPG (SEQ ID NO: 1) peptide can be modified to include lysine (lysine block). This lysine block can be used as the middle block to form the ABA triblock copolymer with the VGVPG (SEQ ID NO: 1) pentapeptide. In these embodiments, the lysine block can be modified to conjugate a molecule or polymer such as phosphoryl choline (PC), poly(ethylene glycol) (PEG), or a bioactive moiety such as nitric oxide generating catalyst or TEMPO as pendant groups. These pendant groups can impart different physical, chemical, or biological properties to the elastin-based polymer.

As one of the properties for the natural elastin materials are usually non-degradable or very slow degradation, degradable linkages can be formed between the peptide blocks so that the newly formed elastin-based materials could be degradable. Any biodegradable polymers described below can be used as the linkage. Some examples of these degradable linkages are poly(lactic acid) (PLA), poly(glycolic acid) (PLGA), polycaprolactone (PCL), poly(3-hydroxybutyric acid) (PHB), poly(4-hydroxybutyrate (P4HB), or combinations of these. Some other clearance mechanisms can be enzymatically degradable (via elastase) or biosoluble when the polymer is sufficiently hydrophilic.

In some embodiments, the elastin-based copolymer is an ABA triblock copolymer where A is a block comprising the VGVPG (SEQ ID NO: 1) peptide and B is a hydrophilic synthetic polymer. Such a synthetic polymer can be, for example, a hydrophilic polymer such as PEG, PVP (poly vinylpyrrolidinone), polyacrylamide, poly(PEG acrylate), poly (HEMA), poly(acrylic acid) or combinations of these polymers.

In some embodiments, the elastin-based copolymer is an ABA triblock copolymer where A is a block comprising the VGVPG (SEQ ID NO: 1) peptide and B is a hydrophilic natural polymer such as protein or peptide. In some embodiments, such a hydrophilic natural polymer can be, for example, collagen or collagen derivative, hyaluronic acid, alginate or combinations of these.

In some embodiments, the elastin-based polymer can include a peptide sequence that promotes proliferation and/or migration of endothelial cells (ECs). Such peptide sequence can be, for example, RGD, cRGD, or EC specific sequences such as SIKVAV (SEQ ID NO: 2), CNP, YIGSRG (SEQ ID NO: 3), mimetics of these sequences, or combinations of these.

In some embodiments, the elastin-based copolymer can include an enzyme susceptible segment(s) or hydrolytically susceptible segment(s). These segment(s) can modify the absorption rate of the polymer so as to allow fine tuning of the absorption rate of the polymer. For example, the absorption rate of the elastin-based polymer can be increased or decreased by the content of these enzyme susceptible segment(s) or hydrolytically susceptible segment(s). As used herein, the term "content" refers to molar ratio of the total units in the enzyme susceptible segment(s) and/or hydrolytically susceptible segment(s) to the total units in the polymer and can range from e.g., above 0 to about 0.5, for example. Examples of enzyme susceptible segment(s) or hydrolytically susceptible segment(s) include, but are not limited to, poly-lactic acid, poly(glycolic) acid, polycaprolactone, poly (alkene succinate), aliphatic-aromatic copolyesters, poly (orthoesters), polyanhydrides, polycarbonates/polyiminocarbonates, or natural degradable polymers including starch, fibre, fibre-starch composites, cellulose, etc.

As used herein, the term "enzyme susceptible segment(s)" refers to a segment(s) that comprises a bonding that can be cleaved by enzyme(s). The term "hydrolytically susceptible segment(s)" refers to a segment(s) that comprises a bonding that can be cleaved by hydrolysis.

Composition of Elastin-Based Polymer

In some embodiments, the elastin-based polymer can be used in a composition for cell therapy carrier. For example, the composition can include the elastin-based polymer, cells such as stem cells and optionally other materials and agents. The composition can be delivered to a dysfunctional part of the body (e.g., an organ such as heart or blood vessel) while the cells are still viable. In some embodiments, the composition can include a pharmaceutically acceptable carrier.

Delivery of the composition can be achieved by any established modes of delivery. Preferably, the delivery can be achieved via delivery from a coating on a medical device (e.g., a stent). In some embodiments, the delivery can be injection or delivery through catheter. In some embodiments, the composition can also be delivered using surgical method such as creating a depot within the muscle and releasing the pharmaceutical agent(s) out of the depot.

In some embodiments, the elastin-based copolymer can be used as hydrogel-like scaffold. For example, one can use it as cell delivery using a depot platform. In some embodiments, a matrix including the polymer described herein can be injected into depots that sit on a carrier platform such as depot stents.

Coating Construct

The elastin-based polymer can form a layer of coating as a topcoat, a matrix layer or a primer layer. The elastin-based polymer coated on a medical device such as a stent according to an established coating process such as dipping, spray or other processes.

In some embodiments, the coating can be formed by dipping in an aqueous solution of the elastin-based polymer. For example, in some embodiments, a solution of an elastin-based polymer described here can be provided. A medical device such as a stent can be dipped in (rinsed) the solution at a temperature below ambient temperature (e.g., 4° C.). The rinsed medical device can be subject to heat treatment at a temperature in the range of about 15° C.-30° C. higher than the lower critical solution temperature (LCST) of the elastin-based polymer to generate a coating with biomimcry effect. FIG. 1 shows stent coated with an elastin-based polymer of the present invention after wet expansion.

A solution of the elastin-based polymer can have a concentration of the polymer ranging from about 1 wt % to about 50 wt %. Preferably, the solution has a concentration of the elastin-based polymer in the range between about 5 wt % and about 30%, for example, about 10 wt %, about 15 wt %, about 20 wt % or about 25 wt %. The solution can include a solvent such as water or a biocompatible organic solvent such as dimethylformamide (DMF), dimethyl sulfoxide (DMSO), dimethyl acetamide (DMAC), methyl ethyl ketone (MEK), ethylene glycol or combinations of these.

In some embodiments, the solvent can be trifluoroethanol (TFE). TFE has a boiling temperature of about 80° C., making the solvent a good solvent for use in coating a medical device. The concentration can be varied and determined according to the molecular weight of the elastin-based polymer for forming the coating. For example, with a elastin-based polymer with a weight average molecular weight about 160K Daltons, a solution of the polymer of about 2 wt % in TFE can be used to form a coating on a medical device using spray coating method at room temperature.

In some embodiments, the solution can be an acidic solution having a pH lower than 7. Where an acidic solution of the elastin-based polymer is used to form the coating on a medical device, medical device rinsed or sprayed with the acidic solution shall be rinsed (or sprayed) with a solution of basic pH (>7) buffered solution. Upon pH increase, the elastin-based polymer will come out of the solution and result in a coating on the medical device. The basic buffered solution can be any basic buffer solution in the art.

The mechanical property of the film cast from elastin-based polymer depends on the solution used in the cast. For example, for elongation of the film, generally a pH>7 coating system will lead to a higher elongation than a neutral or acidic water coating system, and a neutral or acidic water coating system will lead to a higher elongation than a TFE coating system.

In some embodiments, the elastin-based polymer can be coated on a nano- or micro-porous device (e.g., a stent from Blue-Membranes, GmbH, Germany) for controlled release of an agent (e.g., a drug) by modulating the porosity and porous coating thickness. For example, the elastin-based polymer can be coated on the abluminal side of an implantable device as a thin or very thin topcoat. As used herein, the term "thin" or "very thin" refers to a thickness of less than about 1 μm, less than about 500 nm, less than about 100 nm, less than about 50 nm, or less than about 10 nm.

In some embodiments, the elastin-based polymer can be coated on a hydrophobic surface of an implantable device (e.g., a stent). To form this coating, the hydrophobic surface of the implantable device can be modified to include a thin layer of a hydrophilic polymer such as a polymer comprising poly(vinyl alcohol) (PVOH). For example, the surface comprising a fluoropolymer such as a poly(vinylidene fluoride) (SOLEF™) Polymer can be modified by forming a thin layer of PVOH thereon and then forming a thin layer of the elastin-based polymer on top of the PVOH layer. The layer of PVOH can be formed by exposing a hydrophobic surface to a dilute PVOH solution (e.g., a concentration of less than about 5 mass %, less than about 1 mass %, less than about 0.5 mass %, less than about 0.1 mass %, less than about 0.05 or mass % less than about 0.01 mass %) and allowing the PVOH molecule to adsorb onto the hydrophobic surface. Methods of forming a thin PVOH layer on a hydrophobic surface have been described by U.S. application Ser. No. 11/365,392, the teaching of which is incorporated herein by reference in its entirety. As used herein, the term "thin" or "very thin" refers to a thickness of less than about 1 μm, less than about 500 nm, less than about 100 nm, less than about 50 nm, or less than about 10 nm.

Other Biocompatible Polymers

The elastin-based copolymers described herein can be used with other biocompatible polymers. One of the exemplary constructs with other polymers is that the elastin-based copolymer form a topcoat, where the other polymer serves as the controlled release coating and the elastin-based polymer is a topcoat. The biocompatible polymer can be biodegradable (either bioerodable or bioabsorbable or both) or nondegradable and can be hydrophilic or hydrophobic. Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), molecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof. Some examples of elastin protein mimetics include (LGGVG)$_n$ (SEQ ID NO: 4), (VPGVG)$_n$ (SEQ ID NO: 5), Val-Pro-Gly-Val-Gly (SEQ ID NO: 6), or synthetic biomimetic poly(L-glytanmate)-b-poly (2-acryloyloxyethyllactoside)-b-poly(l-glutamate) triblock copolymer.

In some embodiments, the polymer can be poly(ethylene-co-vinyl alcohol), poly(methoxyethyl methacrylate), poly (dihydroxylpropyl methacrylate), polymethacrylamide, aliphatic polyurethane, aromatic polyurethane, nitrocellulose, poly(ester amide benzyl), co-poly-{[N,N'-sebacoyl-bis-(L-leucine)-1,6-hexylene diester]$_{0.75}$-[N,N'-sebacoyl-L-lysine benzyl ester]$_{0.25}$} (PEA-Bz), co-poly-{[N,N'-sebacoyl-bis-(L-leucine)-1,6-hexylene diester]$_{0.75}$-[N,N'-sebacoyl-L-lysine-4-amino-TEMPO amide]$_{0.25}$} (PEA-TEMPO), aliphatic polyester, aromatic polyester, fluorinated polymers such as poly(vinylidene fluoride-co-hexafluoropropylene), poly(vinylidene fluoride) (PVDF), and Teflon™ (polytetrafluoroethylene), a biopolymer such as elastin mimetic protein polymer, star or hyper-branched SIBS (styrene-block-isobutylene-block-styrene), or combinations thereof. In some embodiments, where the polymer is a copolymer, it can be a block copolymer that can be, e.g., di-, tri-, tetra-, or oligo-block copolymers or a random copolymer. In some embodiments, the polymer can also be branched polymers such as star polymers.

In some embodiments, a coating having the features described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Biobeneficial Material

The elastin-based copolymer can optionally used with a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the particles or device by being non-fouling, hemocompatible, actively non-thrombogenic, or antiinflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol)acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), molecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, POLYACTIVE™, and combinations thereof. In some embodiments, a coating described herein can exclude any one of the aforementioned polymers. The term POLYACTIVE™ refers to a block copolymer having flexible poly(ethylene glycol) and poly(butylene terephthalate) blocks (PEGT/PBT). POLYACTIVE™ is intended to include AB, ABA, BAB copolymers having such segments of PEG and PBT (e.g., poly(ethylene glycol)-block-poly(butylene-terephthalate)-block poly(ethylene glycol) (PEG-PBT-PEG).

In a preferred embodiment, the biobeneficial material can be a polyether such as poly(ethylene glycol) (PEG) or polyalkylene oxide.

Bioactive Agents

The elastin-based copolymer can form a coating on a medical device. The coating can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration or proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, mometasone, or combinations thereof. Examples of cytostatic substances include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.). An example of an antiallergic agent is permirolast potassium. Other therapeutic substances or agents which can be appropriate include alpha-interferon, pimecrolimus, imatinib mesylate, midostaurin, bioactive RGD, SIKVAV (SEQ ID NO: 2) peptides, growth factor vascular endothelial growth factor (VEGF), elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Medical Device

As used herein, a medical device can be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, electrodes, pacemaker electrodes, catheters, sensors, endocardial leads (e.g., FINELINE and ENDOTAK, available from Abbott Vascular, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers or bioabsorbable metals such as magnesium could also be used with the embodiments of the present invention. In some embodiments, the device is a bioabsorbable stent.

Method of Use

In accordance with embodiments of the invention, a medical device having a coating that includes the elastin-based polymer described herein can be used for treating, preventing or ameliorating a medical condition. Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents can be placed in a wide array of blood vessels, both arteries and veins. In some embodiments, the device described herein can be in dialysis, as grafts, or fistulae.

Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described features can then be expanded at the desired area of treatment. A post-insertion angiogram can also be utilized to confirm appropriate positioning.

Example 1

Studies on Integrity of Coatings Formed of Elastin-Based Polymer

Study Design

1% of an elastin-based copolymer (B-9 polymer) in TFE was coated onto Vision 18 mm small stents, available from Abbott Vascular, Santa Clara, Calif., with a thickness of about 4 µm. Coated stents were then sent out for E-beam at 25 kGy. The following tests were then conducted on these stents:

1) Simulated use test—stent was expanded in PVA vessel following by 37 C distilled water flowing through the stent for 1 hour. The water flow rate is 50 ml/min.

2) Particulate counting—The particulate counting test was done in the similar format as that for simulated use test. The stent was expanded in a Tygon vessel. Distilled water was continuously flowing through the stent for 1 hour. The water flow rate is 100 ml/min. Any particulate generated was counted by a detector at each minute interval. The particulate size set was 10-25 µm, 25-165 µm, and >165 µm (these are based on USP and also set for Xience V product). In this experiment, Xience V was used as the control group.

3) Chandler loop study, bare metal vision stent and Xience V stent were used as control. The whole porcine blood was flowing through the stent (relative movement) for 2 hours. The theoretical flow rate is about 75 ml/min.

As used herein, ID means lumen surface, which is exposed to water during simulated use test; OD is the abluminal surface, which was against the PVA tubing during the test. Xience V is a coating formed of PVDF-HFP polymer (fluoronated polymer) with everolimus. BMS stands for "bare metal stent."

Results Summary

After simulated use test, the most of OD surface was not affected by the simulated use. The particulate count data showed similar results as compared to the control group (Xience V) and they all passed the Xience V specification (Table 1). The stents were also examined using SEM after the particulate count test.

TABLE 1

Particulate Count Result

| | | 5 min | 10 min | 20 min | 40 min | 60 min |
|---|---|---|---|---|---|---|
| | | | | 10-25 um | | |
| Blank | Ave | 34 | 55 | 73 | 108 | 115 |
| | SD | 30 | 60 | 85 | 87 | 94 |
| Control | Ave | 99 | 100 | 101 | 103 | 105 |
| | SD | 146 | 146 | 146 | 145 | 148 |
| B-9 | Ave | 107 | 108 | 113 | 138 | 153 |
| | SD | 118 | 121 | 120 | 121 | 127 |
| | | | | 25-165 um | | |
| Blank | Ave | 35 | 91 | 101 | 172 | 274 |
| | SD | 34 | 80 | 92 | 147 | 247 |
| Control | Ave | 20 | 20 | 20 | 20 | 20 |
| | SD | 33 | 33 | 33 | 33 | 33 |
| B-9 | Ave | 20 | 21 | 23 | 24 | 26 |
| | SD | 28 | 30 | 33 | 32 | 32 |
| | | | | >165 um | | |
| Blank | Ave | 3 | 8 | 8 | 17 | 17 |
| | SD | 6 | 13 | 14 | 14 | 14 |
| Control | Ave | 5 | 5 | 5 | 5 | 5 |
| | SD | 8 | 8 | 8 | 8 | 8 |
| B-9 | Ave | 7 | 7 | 7 | 7 | 7 |
| | SD | 12 | 12 | 12 | 12 | 12 | n=3 for blank, n=6 for Xience control, n=6 for B-9 coating
Criteria for Xience V
Bin 10 <= 2100/per sample
Bin 25 <= 200/per sample
Ben 165 <= 200/per sample The chandler loop study showed B-9 coated stents had less thrombosis than bare metal Vision stent. B-9 coated stents also had more thrombosis than Xience stents. But they are all very clean. The SEM image for the stent after chandler loop study showed no polymer dissolving or peeling on ID.

SEM Results

Figure 2:
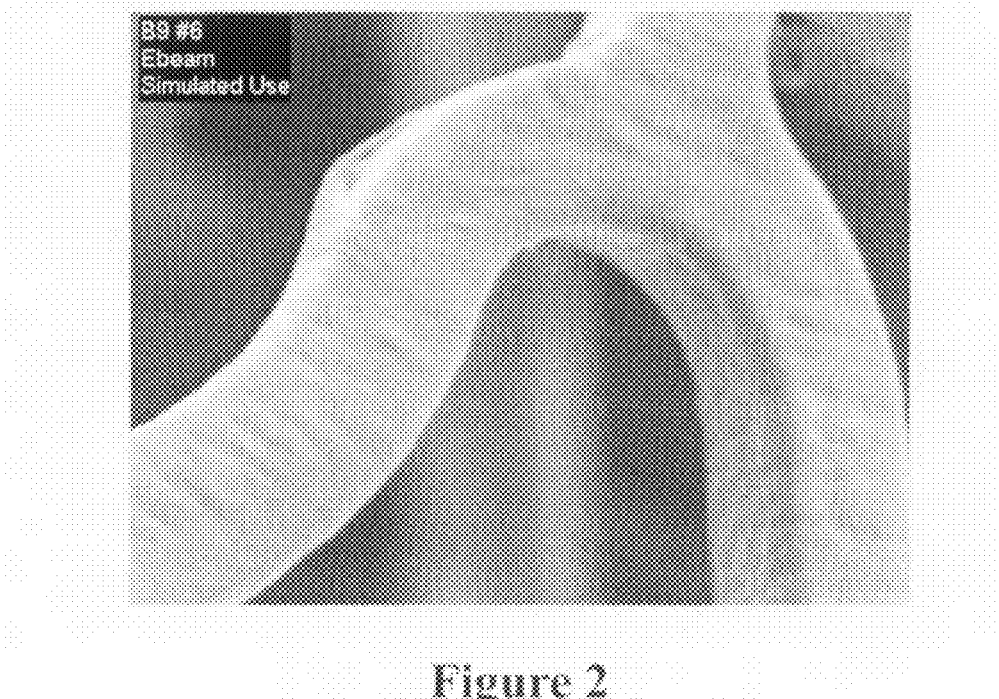
FIG. 2 shows the OD of B9 coated stent after simulated use test.

The coatings formed in this Example were subjected to scanning electron mamograph (SEM) studies (FIGS. 1-2).

FIG. 1 shows that B-9 coating is crimping/icy hot onto catheters, followed after E-beam. It is noted that the surface is rough due to the choice of solvent.

FIG. 2 shows the OD of B9 coated stent after simulated use test. The coating is still holding on the stent. It is also noted that the surface is smoother than that on the control sample in FIG. 1.

Chandler Loop Study Result

The coatings formed above were subjected to Chandler loop study. Some representative results are shown in FIGS. 3-6.

Figure 3:
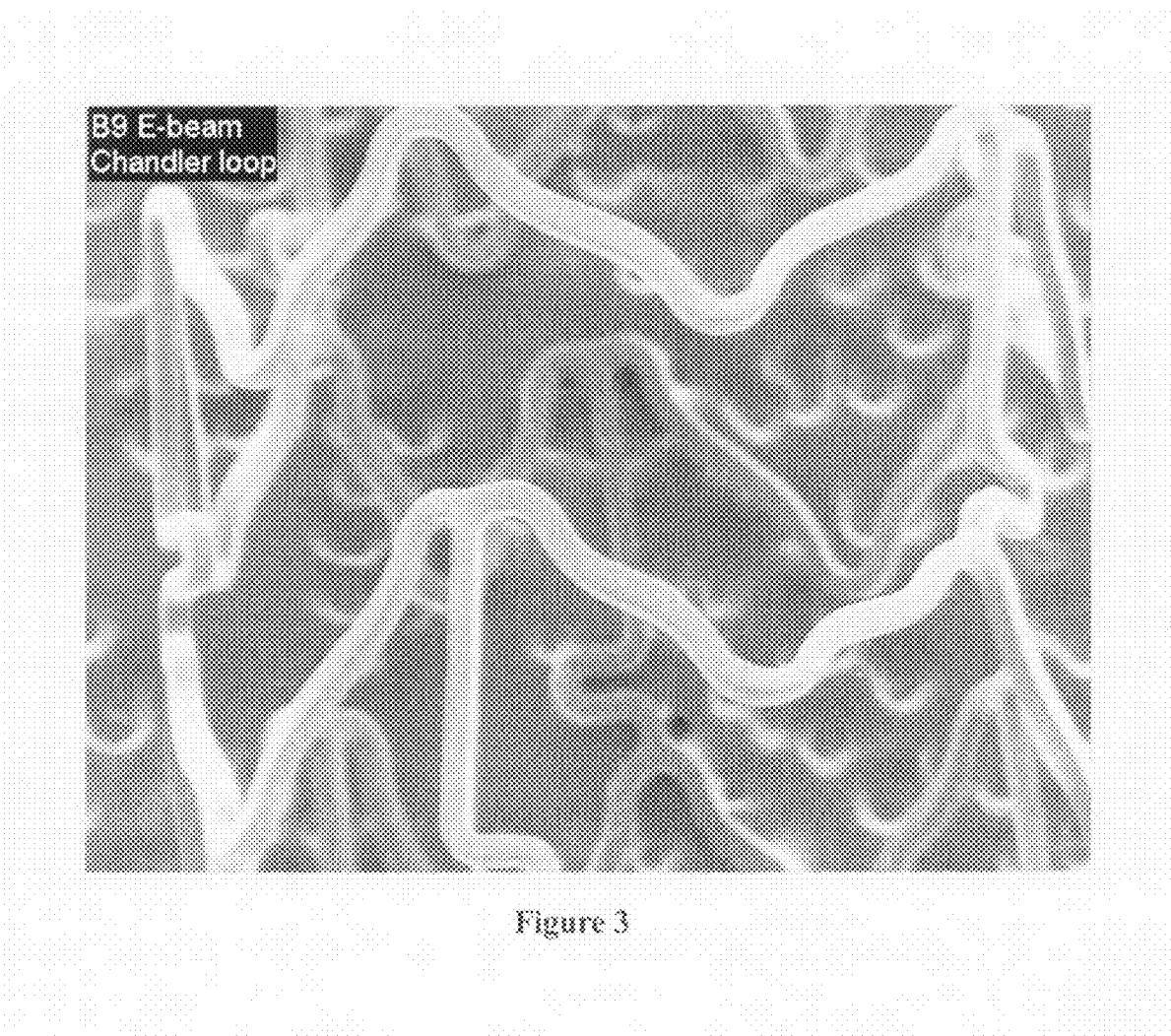
FIG. 3 shows a B-9 coated stent after chandler loop test.

FIG. 3 shows a B-9 coated stent after chandler loop test. The coating is not impacted by 2-hour blood flow.

Figure 4:
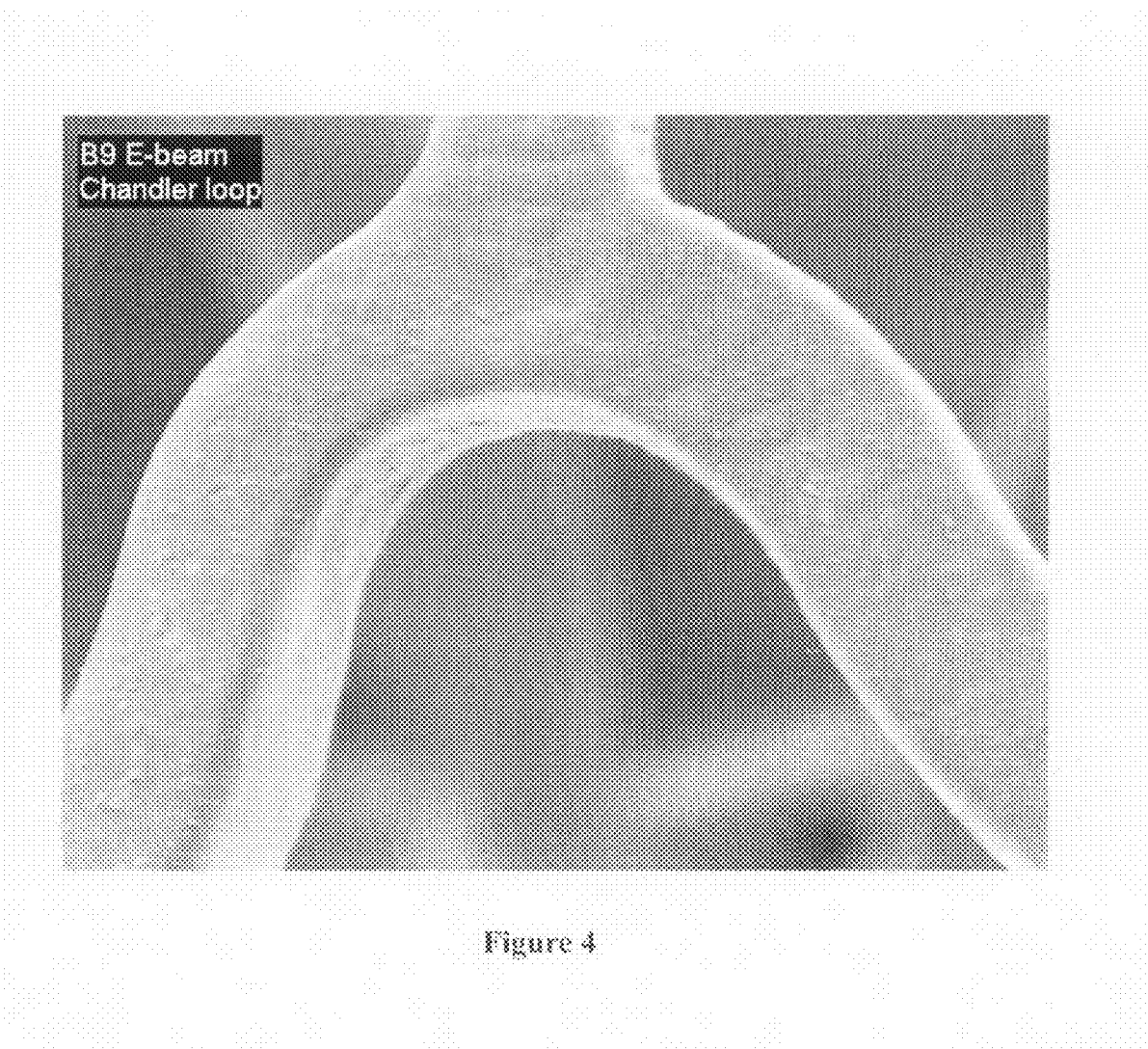
FIG. 4 shows a typical OD surface of B-9 coated stent after chandler loop test.

FIG. 4 shows a typical OD surface of B-9 coated stent after chandler loop test. There is no peeling or cracking at the high strain area. The debris left on the surface are from the blood. But it is also seen that the surface has been smoothen as comparing to the control in FIG. 1.

Figure 5:
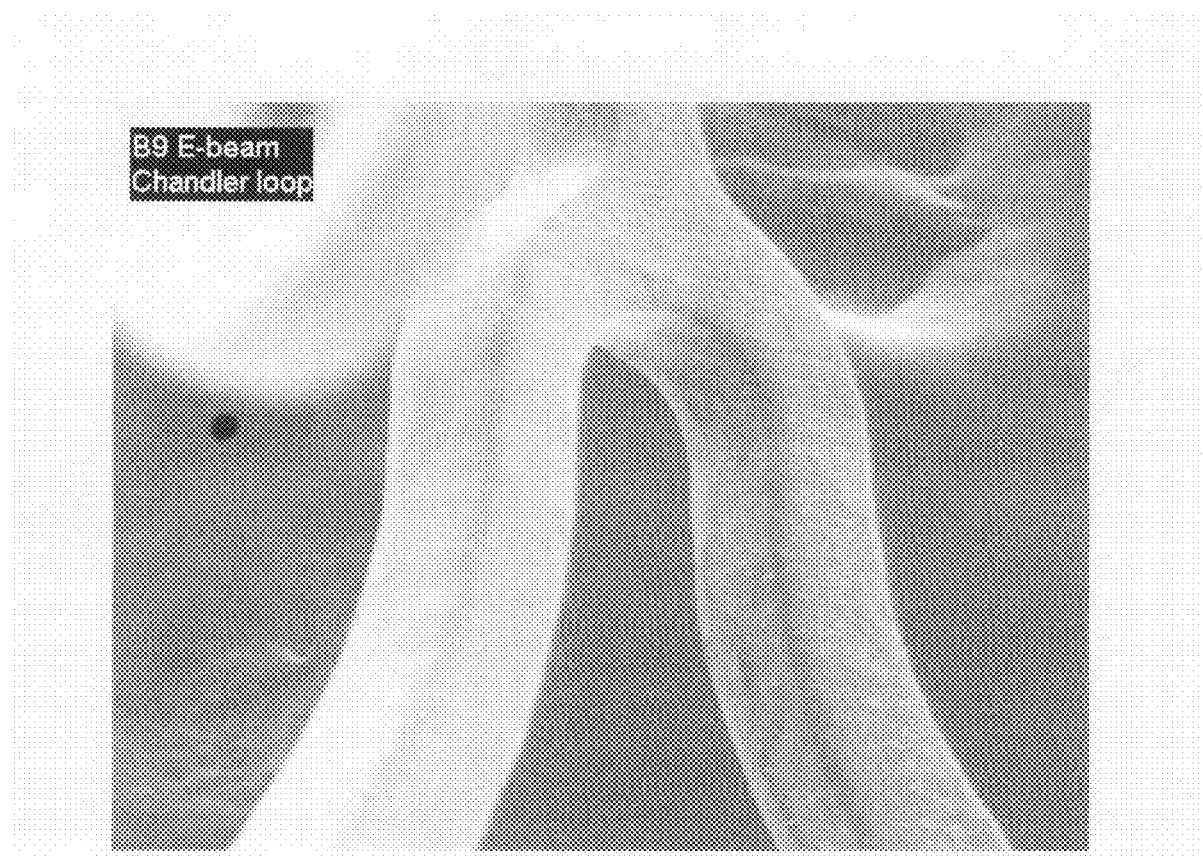
FIG. 5 shows a typical ID surface of B-9 coated stent after chandler loop study.

FIG. 5 shows a typical ID surface of B-9 coated stent after chandler loop study. The stent was still covered by polymer and there was so sign of polymer peeling and dissolving.

Figure 6:
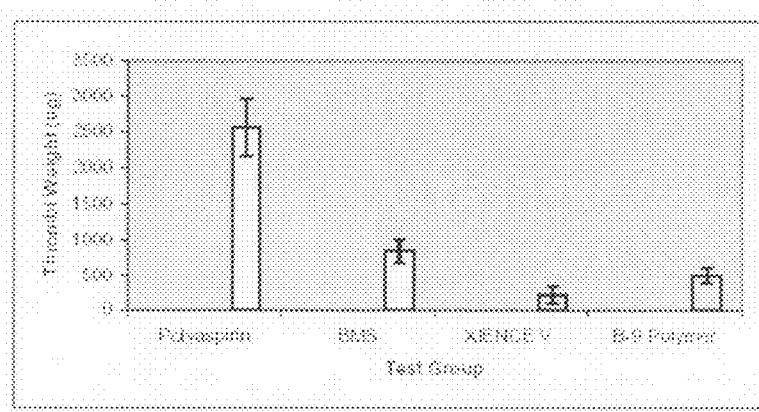
FIG. 6 shows thrombi weight of different type of coatings.

FIG. 6 shows thrombi weight of different type of coatings.

In FIG. 6, the statistics parameters are shown below:

| | |
|---|---|
| Xience vs BMS: | p value = 0.0025 |
| B9 vs BMS: | p value = 0.0678 |
| B9 vs Xience: | p value = 0.0584 |

Discussions

B-9 polymer was able to be coated onto Vision stents with good coating integrity after expansion. The particulate count results showed comparable results as comparing to the Xience V control and all passed the Xience V particulate count specification. The chandler loop results did not show any adverse effect on thrombosis on this coating. A higher thrombosis than Xience control probably is due to the fact that Xience coat had very low surface energy that, by nature, does not adhere proteins. The less thrombosis of B-9 coating than bare metal Vision stents is positive.

The coating after 2 hours in chandler loop (flow rate as 75 ml/min) showed that the coating was not impacted at all, without any cracking at high strain area. This result indicates that the B-9 coating behave differently in blood as comparing in water.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device comprising a topcoat of a copolymer on top of a coating, wherein the copolymer comprises an elastin pentapeptide VGVPG (SEQ ID NO:1) (A) and a hydrophilic block (B),
wherein the coating comprises a layer of a hydrophobic polymer underneath a thin layer of a polymer comprising poly(vinyl alcohol) (PVOH), and the topcoat on top of the thin layer of polymer comprising PVOH.

2. The medical device of claim 1, wherein the copolymer is an ABA copolymer.

3. The medical device of claim 1, wherein the hydrophilic block comprises lysine.

4. The medical device of claim 2, wherein the hydrophilic block comprises lysine.

5. The medical device of claim 2, wherein the hydrophilic block comprises a synthetic polymer.

6. The medical device of claim 2, wherein the hydrophilic block comprises a natural polymer.

7. The medical device of claim 2, wherein the hydrophilic block is a variant of the VGVPG obtained by replacing one amino acid in VGVPG (SEQ ID NO:1) with another amino acid.

8. The medical device of claim 4, wherein the copolymer further comprises a phosphoryl choline (PC) or poly(ethylene glycol) (PEG) pendant group,
wherein the PC or PEG is conjugated to the copolymer via lysine in the hydrophilic block.

9. The medical device of claim 5, wherein the synthetic polymer is selected from PEG, PVP (poly vinylpyrrolidinone), polyacrylamide, poly(PEG acrylate), poly (HEMA), poly(acrylic acid) and combinations of these.

10. The medical device of claim 6, wherein the natural polymer is selected from collagen, collagen derivative, hyaluronic acid, alginate and combinations of these.

11. The medical device of claim 1, wherein the copolymer further comprises an ANP peptide, a BNP peptide, an RGD peptide, a cRGD peptide, a SIKVAV peptide (SEQ ID NO: 2), a CNP peptide, a YIGSRG peptide (SEQ ID NO: 3), a hydrolytic segment, or a combination thereof.

12. The medical device of claim 2, wherein the copolymer further comprises an ANP peptide, a BNP peptide, an RGD peptide, a cRGD peptide, a SIKVAV peptide (SEQ ID NO: 2), a CNP peptide, a YIGSRG peptide (SEQ ID NO: 3), a hydrolytic segment, or a combination thereof.

13. The medical device of claim 1, wherein the copolymer further comprises a biodegradable linkage between the A and the B block.

14. The medical device of claim 1, wherein the copolymer further comprises a biodegradable linkage selected from poly(lactic acid) (PLA), poly(glycolic acid) (PLGA), polycaprolactone (PCL), poly(3-hydroxybutyric acid) (PHB), poly(4-hydroxybutyrate (P4HB), and combinations of these.

15. The medical device of claim 1, wherein the hydrophobic polymer comprises a polymer of a fluoroolefin.

16. The medical device of claim 15, wherein the hydrophobic polymer is poly(vinylidene fluoride) (PVDF).

17. The medical device of claim 1, wherein the layer of the hydrophobic polymer further comprises a bioactive agent.

18. The medical device of claim 1, wherein the coating comprises a bioactive agent selected from the group consisting of paclitaxel, docetaxel, estradiol, 17-beta-estradiol, nitric oxide donors, super oxide dismutases, super oxide dismutase mimetics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, vascular endothelial growth factor (VEGF), and prodrugs, co-drugs, and combinations of these.

19. The medical device of claim 17, wherein the bioactive agent is selected from the group consisting of paclitaxel, docetaxel, estradiol, 17-beta-estradiol, nitric oxide donors, super oxide dismutases, super oxide dismutase mimetics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, vascular endothelial growth factor (VEGF), and prodrugs, co-drugs, and combinations of these.

20. The medical device of claim 1, wherein the coating comprises a bioactive agent comprising a combination of an anti-proliferative and an anti-inflammatory.

21. The medical device of claim 17, wherein the bioactive agent comprises a combination of an anti-proliferative and an anti-inflammatory.

22. The medical device of claim 18, which is a stent.

23. The medical device of claim 19, which is a stent.

24. A method of treating, preventing or ameliorating a disorder in a patient comprising implanting in the patient the medical device of claim 18, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

25. A method of treating, preventing or ameliorating a disorder in a patient comprising implanting in the patient the medical device of claim 19, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

\* \* \* \* \*